(12) United States Patent
Liu et al.

(10) Patent No.: US 7,459,070 B2
(45) Date of Patent: *Dec. 2, 2008

(54) AUTOMATED PARALLEL CAPILLARY ELECTROPHORESIS SYSTEM WITH HYDRODYNAMIC SAMPLE INJECTION

(75) Inventors: Changsheng Liu, State College, PA (US); Thomas E. Kane, State College, PA (US); Qingbo Li, State College, PA (US)

(73) Assignee: Applied Biosystems Inc., Foster City, CA (US)

( * ) Notice: Subject to any disclaimer, the term of this patent is extended or adjusted under 35 U.S.C. 154(b) by 364 days.

This patent is subject to a terminal disclaimer.

(21) Appl. No.: 11/204,773

(22) Filed: Aug. 15, 2005

(65) Prior Publication Data

US 2006/0091011 A1    May 4, 2006

Related U.S. Application Data

(63) Continuation of application No. 09/388,125, filed on Aug. 31, 1999, now Pat. No. 6,352,633, and a continuation of application No. 10/011,977, filed on Dec. 11, 2001, now Pat. No. 6,953,521.

(51) Int. Cl.
  *G01N 27/447* (2006.01)
  *G01N 27/453* (2006.01)
(52) U.S. Cl. .............................. 204/453; 204/603
(58) Field of Classification Search ......... 204/450–455, 204/600–605
  See application file for complete search history.

(56) References Cited

U.S. PATENT DOCUMENTS 5,085,757 A    2/1992   Karger et al.

(Continued)

FOREIGN PATENT DOCUMENTS

DE    G9011484.1    * 11/1990

(Continued)

OTHER PUBLICATIONS

International Search Report for International Application No. PCT/US97/17792 Jan. 26, 1998.*

(Continued)

*Primary Examiner*—Alex Noguerola
(74) *Attorney, Agent, or Firm*—McQuaide, Blasko, Fleming & Faulkner, Inc.

(57) ABSTRACT

An automated capillary zone electrophoretic system is disclosed. The system employs a capillary cartridge having a plurality of capillary tubes. The cartridge has a first array of capillary ends projecting from one side of a plate. The first array of capillary ends are spaced apart in substantially the same manner as the wells of a microtitre tray of standard size. This allows one to simultaneously perform capillary electrophoresis on samples present in each of the wells of the tray. The system includes a stacked, dual carrousel arrangement to eliminate cross-contamination resulting from reuse of the same buffer tray on consecutive executions from electrophoresis. The system also has a container connected to the detection end of the capillaries. The container is provided with valving which facilitate cleaning the capillaries, loading buffer into the capillaries, introducing samples to be electrophoresed into the capillaries, and performing capillary zone electrophoresis on the thus introduced samples.

20 Claims, 8 Drawing Sheets

U.S. PATENT DOCUMENTS

| | | |
|---|---|---|
| 5,198,091 A | 3/1993 | Burolla et al. |
| 5,207,886 A | 5/1993 | Lauer |
| 5,235,409 A | 8/1993 | Burgi et al. |
| 5,240,585 A | 8/1993 | Young et al. |
| 5,274,240 A | 12/1993 | Mathies et al. |
| 5,277,780 A | 1/1994 | Kambara |
| 5,290,418 A | 3/1994 | Menchen et al. |
| 5,302,264 A * | 4/1994 | Welch et al. .............. 204/452 |
| 5,332,480 A | 7/1994 | Datta et al. |
| 5,332,481 A | 7/1994 | Guttman |
| 5,356,525 A | 10/1994 | Goodale et al. |
| 5,413,686 A | 5/1995 | Klein et al. |
| 5,417,925 A | 5/1995 | Goodale et al. |
| 5,436,130 A | 7/1995 | Mathies et al. |
| 5,447,611 A | 9/1995 | Lauer |
| 5,498,324 A | 3/1996 | Yeung et al. |
| 5,516,409 A | 5/1996 | Kambara |
| 5,582,705 A | 12/1996 | Yeung et al. |
| 5,605,666 A | 2/1997 | Goodale et al. |
| 5,635,050 A | 6/1997 | Pentoney, Jr. et al. |
| 5,730,850 A | 3/1998 | Kambara et al. |
| 5,916,428 A | 6/1999 | Kane et al. |
| 6,027,627 A | 2/2000 | Li et al. |
| 6,352,633 B1 * | 3/2002 | Liu et al. .............. 204/453 |
| 6,766,817 B2 | 7/2004 | da Silva |
| 6,953,521 B2 * | 10/2005 | Liu et al. .............. 204/453 |

FOREIGN PATENT DOCUMENTS

| | | |
|---|---|---|
| EP | 0 257 855 | 3/1988 |
| EP | 0 723 149 | 7/1996 |
| GB | 2 113 903 | 8/1983 |
| WO | WO 89/04966 | 6/1989 |
| WO | WO 94/29712 | 12/1994 |
| WO | WO 94/29713 | 12/1994 |
| WO | WO 99/00664 | 1/1999 |

OTHER PUBLICATIONS

International Search Report for International Application No. PCT/US98/13667 Oct. 30, 1998.*

Written Opinion in corresponding International Application No. PCT/US98/13667 (WO 99/00664).

* cited by examiner

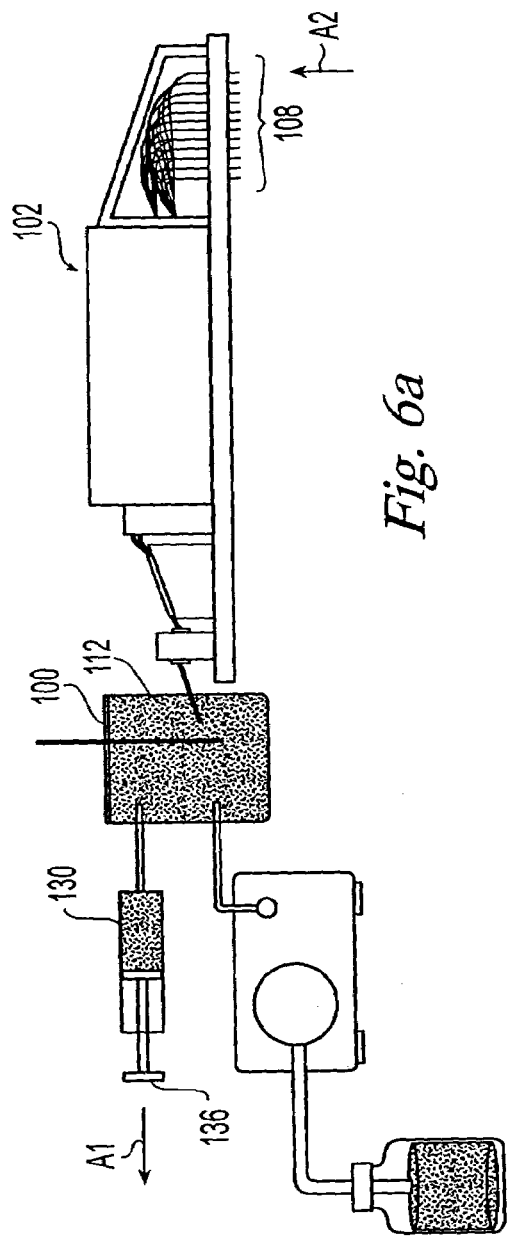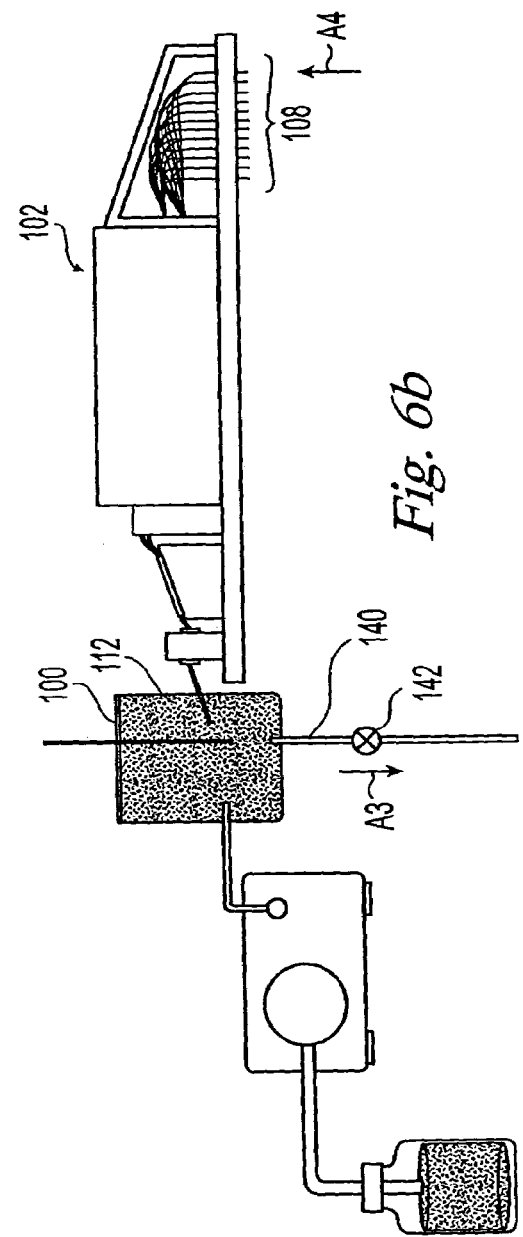

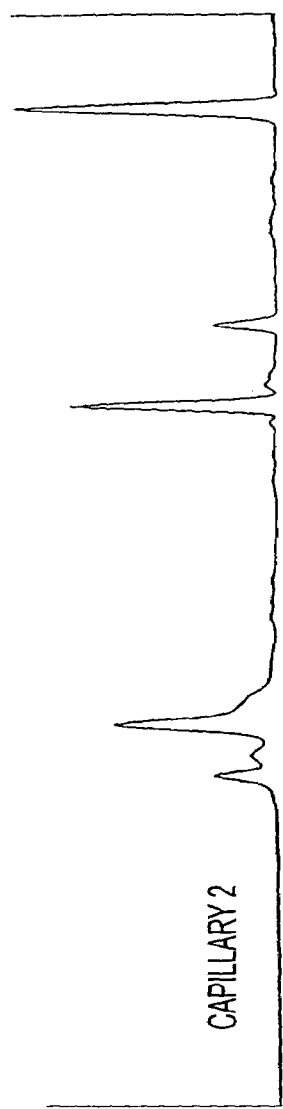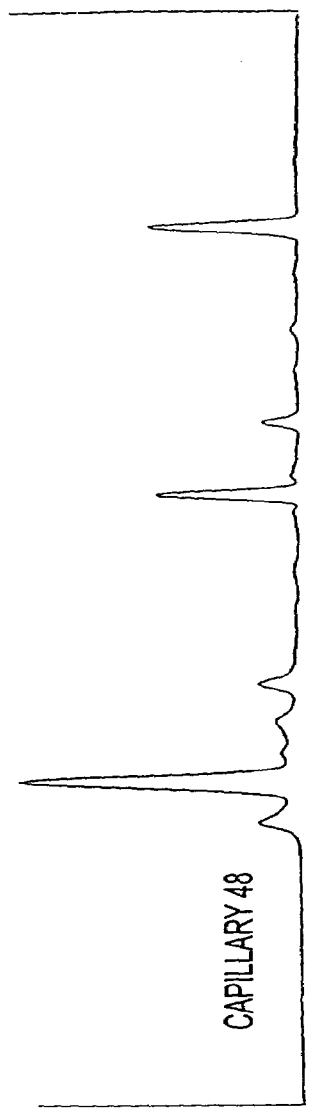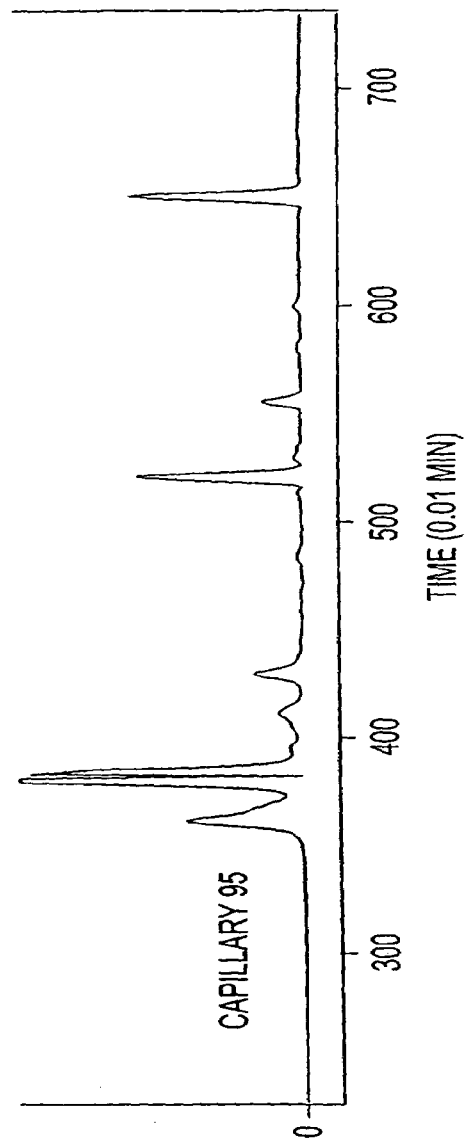

AUTOMATED PARALLEL CAPILLARY ELECTROPHORESIS SYSTEM WITH HYDRODYNAMIC SAMPLE INJECTION

RELATED APPLICATIONS

This application is a Continuation under 35 U.S.C. § 120 of U.S. patent application Ser. No. 09/388,125, filed Aug. 31, 1999, now U.S. Pat. No. 6,352,633, and Ser. No. 10/011,977, filed Dec. 11, 2001, now U.S. Pat. No. 6,953,521.

TECHNICAL FIELD

This invention relates to an automated apparatus for performing multiplexed Capillary Electrophoresis. It is especially useful in an automated Capillary Zone Electrophoresis (CZE) system for loading samples into a plurality of capillaries from wells of commercially available, microtitre trays of standard size.

BACKGROUND

The contents of commonly-owned U.S. patent application Ser. No. 09/105,988, which issued as U.S. Pat. No. 6,027,627 and also was published as WO 99/00664 are incorporated by reference to the extent necessary to understand the present invention. This reference discloses an automated apparatus for capillary electrophoresis.

FIG. 1 illustrates a prior art automated electrophoretic apparatus discussed in the above-referenced patent application for capillary electrophoresis. The apparatus includes a light source 452, a processor/controller 404, a dual carrousel arrangement having an upper carrousel 601 and a lower carrousel 602 which are aligned and spaced apart along a common axis and operated by a rotor 604, a DC motor 605 having a movable member 603 to move a tray 214 place on one of the carrousels along a common axis toward or away from an array of capillary ends belonging to a capillary cartridge 300, a detector 408 for detecting, at a window region 130 of the capillaries, the fluorescence emitted by samples migrating along the capillaries, and a computer monitor 406 to view the results of the migration. An electrophoretic medium, such as a gel, can be introduced into the capillaries via a conduit 606 in preparation for an electrophoretic run.

FIG. 2 illustrates a prior art plumbing system in accordance with the above-identified reference, for performing capillary electrophoresis using the device of FIG. 1. In particular, FIG. 2 shows the integration of a gel syringe 804 and an HPLC wash solvent system 807 into the solvent/gel delivery module. A solvent manifold 850 connects three inlets from the feeder tubes 806 of the solvent containers 801, 802, 803 to an outlet. Feeder tubes 806 from the solvent containers 801, 802, 803 are connected to the inlets of the solvent manifold 850 by tubing 860. The controller 404 pictured in FIG. 1 controls the solvent manifold 850 to select solvent from one of the three solvent containers 801, 802, 803. The inlet of the HPLC pump 807 is connected to the outlet of the solvent manifold 850 by tubing 861 and the outlet of the HPLC pump 807 is connected to an inlet of a valve manifold 851 by tubing 862.

The valve manifold 851 connects two inlets and an outlet. One inlet of the valve manifold 851 is connected to the gel syringe 804 by tubing 863 and the other inlet of the valve manifold 851 is connected to the outlet of the HPLC pump 807. The outlet of the valve manifold 851 is connected to the solvent/gel input port 606 by tubing 864. The controller 404 pictured in FIG. 11 causes the valve manifold 851 to select either the inlet connected to the gel syringe 804 or the inlet connected to the HPLC pump 807. In this manner, gel and solvents are delivered to the capillary cartridge 909 in preparation for capillary gel electrophoresis of samples in microtitre tray 852.

In the preferred embodiment, the tubing connecting the feeder tubes 806 of the solvent containers 801, 802, 803 to the inlets of the solvent manifold 850 is standard teflon tubing with a diameter of ⅛ inches. The tubing 861 connecting the outlet of the solvent manifold 850 to the inlet of the HPLC pump 807 is PEEK tubing with a diameter of 1/16 inches. The tubing 861 connecting the outlet of the solvent manifold 850 to the inlet of the HPLC pump 807, the tubing 862 connecting the outlet of the HPLC pump 807 to an inlet of the valve manifold 851, the tubing 863 connecting the gel syringe 804 to an inlet of the valve manifold 851 and the tubing 864 connecting the outlet of the valve manifold 851 to the solvent/gel input port are PEEK tubing with a diameter of 1/16 inches.

FIG. 3 illustrates a preferred embodiment of capillary cartridge 1180 in accordance with the above-identified application. In this embodiment, the capillary tubes run from their first ends 1188 disposed in an electrode/capillary array 1181. The capillary tubes then run inside multilumen tubing 1183. The multilumen tubing is taught in detail in U.S. patent application Ser. No. 08/866,308, which is incorporated by reference herein. The multilumen tubing 1183 is held firmly in place by tubing holders 1185. The capillary tubes, without the protection the multilumen tubing, pass through an optical detection region 1187. Beyond the optical detection region 1187, the capillary tubes have a common termination and are bundled together and cemented into a high pressure T-shaped fitting 1182 made from electrically conductive material, which, during electrophoresis, is connected to electrical ground.

The tubing holders 1185 and the T-fitting 1182 are fixed to a cartridge base 1186. The cartridge base 1186 is made from polycarbonate plastic for its dielectric characteristic. The base 1186 in turn is removably attached to a shuttle 1179 which includes a set of rail couplings 1184 protruding from its bottom. These rail couplings 1184 are arranged so that they fit on to a railing system (not shown in FIG. 18) of the apparatus in FIG. 1. The railing system allows the shuttle 1184 to move between an in position and out position. The base 1186 is detached from the shuttle 1179 so that the cartridge 1180 is disposed (or cleaned) and a new (or cleaned) capillary cartridge is attached when the shuttle 1179 is in its out position. The combination of the railing system and the shuttle 1179 allows the newly attached capillary cartridge to be repeatedly located at the same position as that of the disposed capillary cartridge in relation to a camera and a laser (not shown in FIG. 3) when the shuttle 1179 is in its in position. In a preferred embodiment, the shuttle 1179 extends the length of the base 1186 with an opening to accommodate the electrode/capillary array 1181; the shuttle 1179 is attached to the base 1186 by a plurality of removable fasteners 1178.

The prior art plumbing system of FIG. 2 and T-fitting of FIG. 3 are best suited for capillary gel electrophoresis. In capillary gel electrophoresis, the gel is fairly viscous, on the order of 50,000 centi-poise. This requires a system which can create pressure sufficient to load gel into the capillaries in preparation for a capillary electrophoresis run, and sufficient to expel the gel from the capillaries during reconditioning.

In contrast to the gels that are used in capillary gel electrophoresis, buffers are used to load the capillaries in capillary zone electrophoresis (CZE). These buffers have a viscosity on the order of that of water, i.e., about 1 centi-poise. While the low viscosity of buffers has the advantage of not needing high pressure to load and unload the electrophoretic medium, CZE with buffers does have the disadvantage of capillary siphoning. Capillary siphoning is characterized by the buffer solution at one end of the capillaries being completely drawn into the capillaries, thereby depleting the buffer at that one end. Like siphoning of any tubing, this problem occurs when the two ends of the capillaries terminate at different heights. The obvious solution to this problem is to ensure that opposite ends of the capillaries are maintained at the same level. This, however, is less than an ideal solution.

SUMMARY OF THE INVENTION

The present invention is directed to an automated parallel capillary zone electrophoresis (CZE) system. The CZE system of the present invention is realized by modifying the prior art capillary gel electrophoresis (CGE) system of the above-reference prior art. More particularly, the present invention is principally realized by modifying the plumbing at the ends of the capillaries towards which samples in the capillaries migrate.

BRIEF DESCRIPTION OF THE DRAWINGS

FIG. 4a shows a preferred embodiment of the present invention for performing capillary zone electrophoresis;

FIG. 4b shows a sequence of valve settings for the embodiment of FIG. 4a;

FIGS. 6a & 6b show two versions of a third embodiment of a system in accordance with the present invention;

FIGS. 8a, 8b & 8c shows intensity plots for experimental samples migrating in three of the 96 capillaries.

DETAILED DESCRIPTION OF THE PREFERRED EMBODIMENT

The contents of commonly-owned, aforementioned U.S. patent application Ser. No. 09/105,988, which issued as U.S. Pat. No. 6,027,627 and also was published as WO 99/00664, are incorporated by reference to the extent necessary to understand the present invention.

Figure 1:
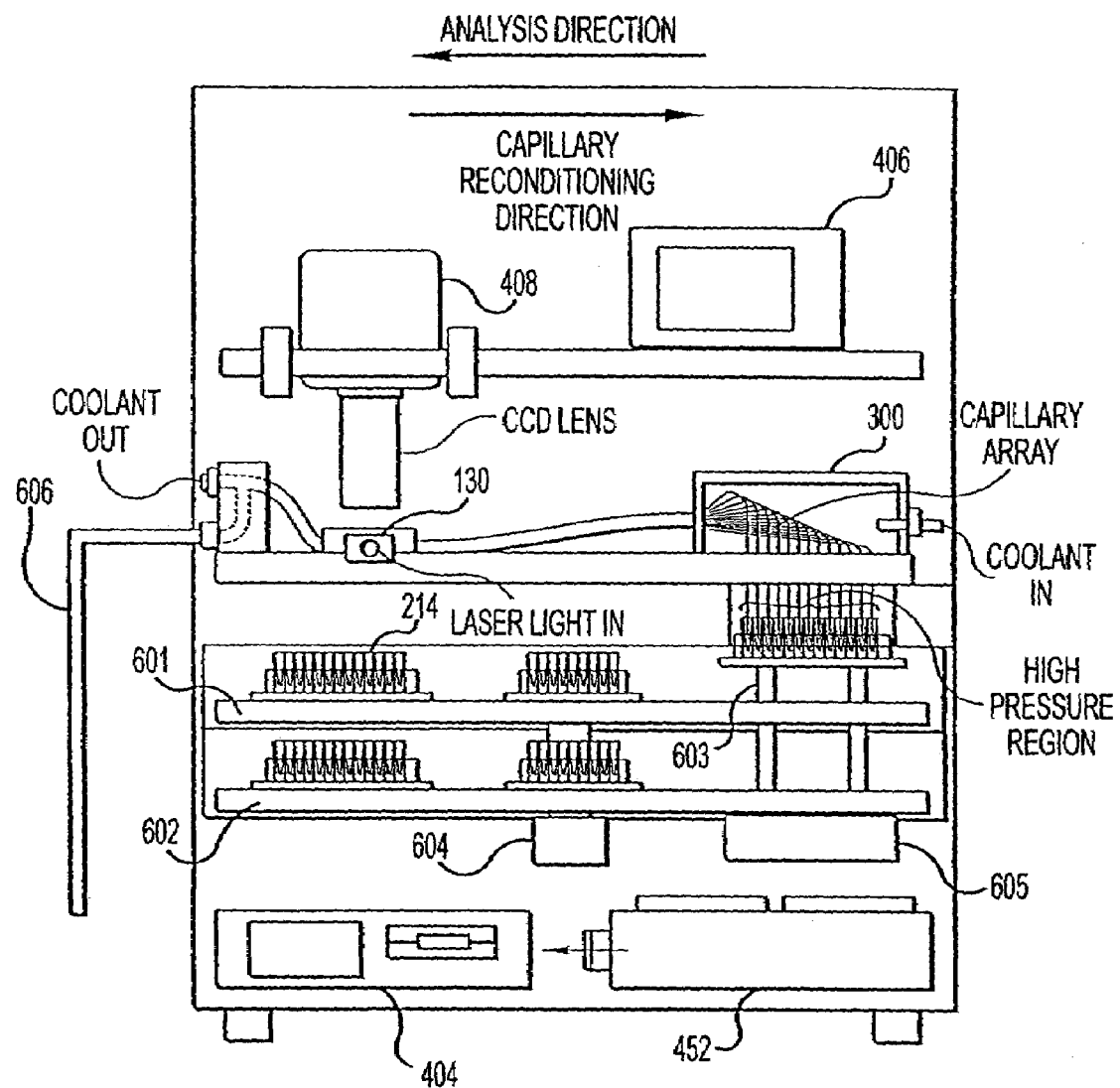
FIG. 1 is a side view of a prior art automated capillary electrophoresis system suitable for capillary gel electrophoresis.
Figure 2:
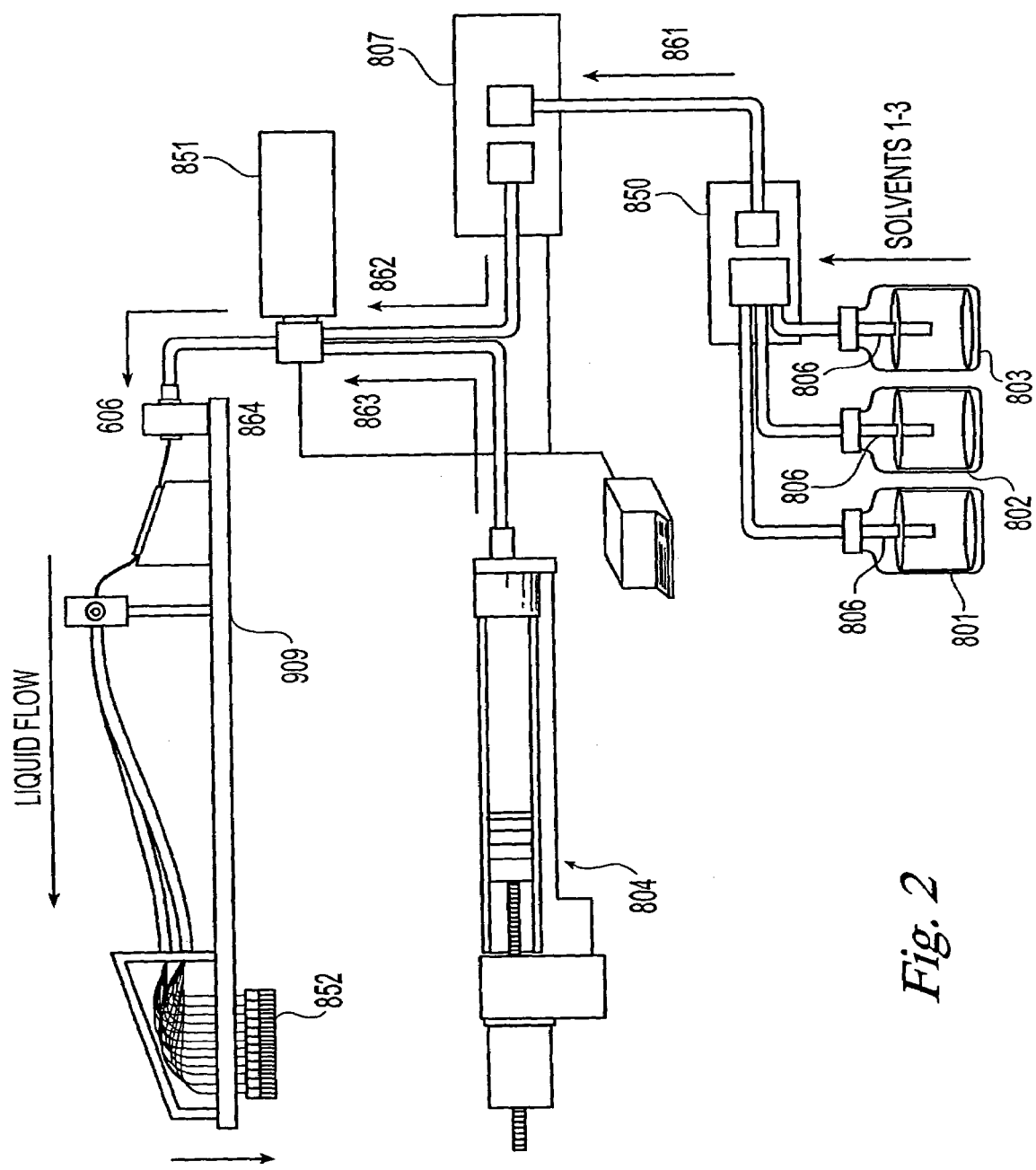
FIG. 2 illustrates a prior art plumbing system for the electrophoresis system of FIG. 1.
Figure 3:
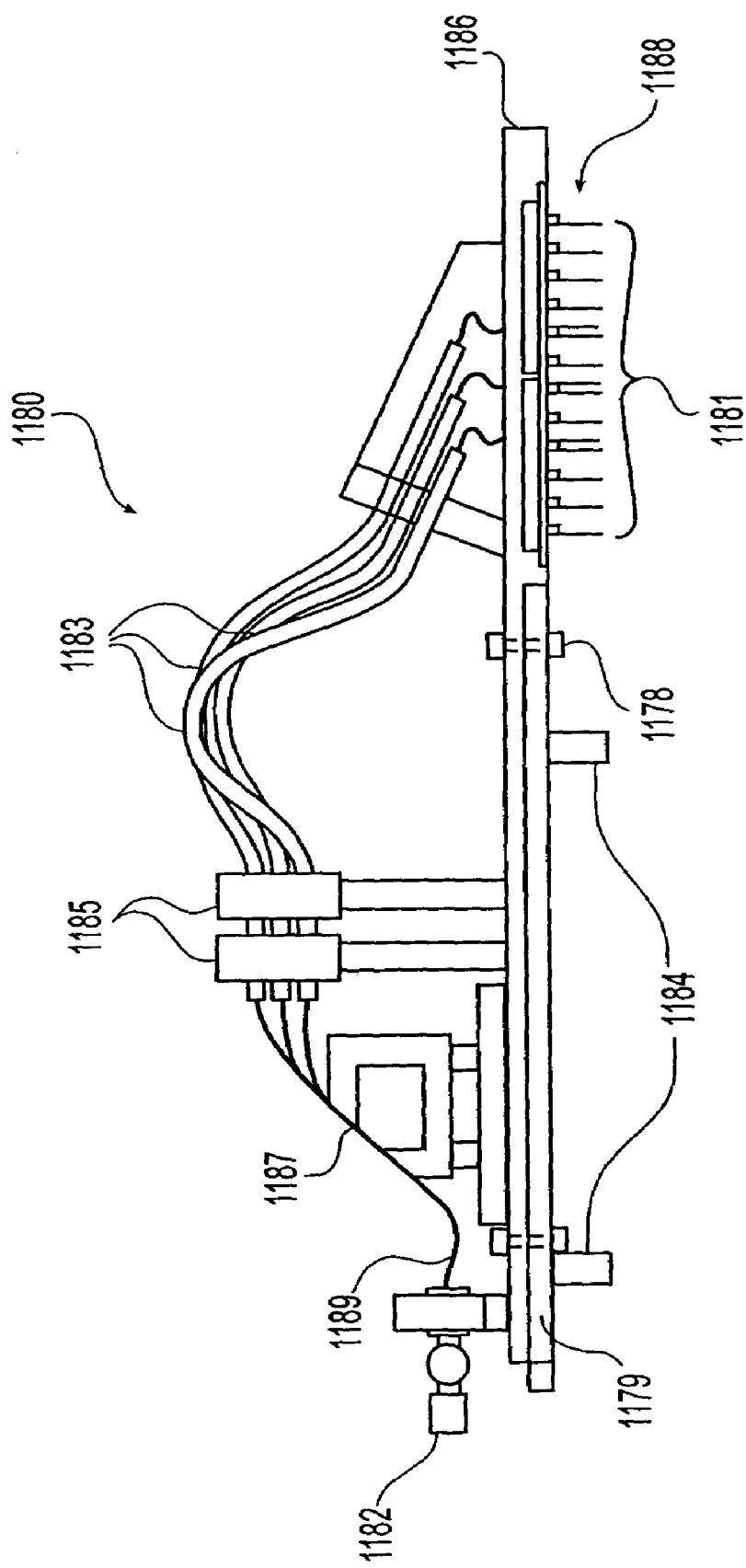
FIG. 3 is a side view of a prior art capillary cartridge for use with the electrophoresis system of FIGS. 1 and 2.
Figure 4:
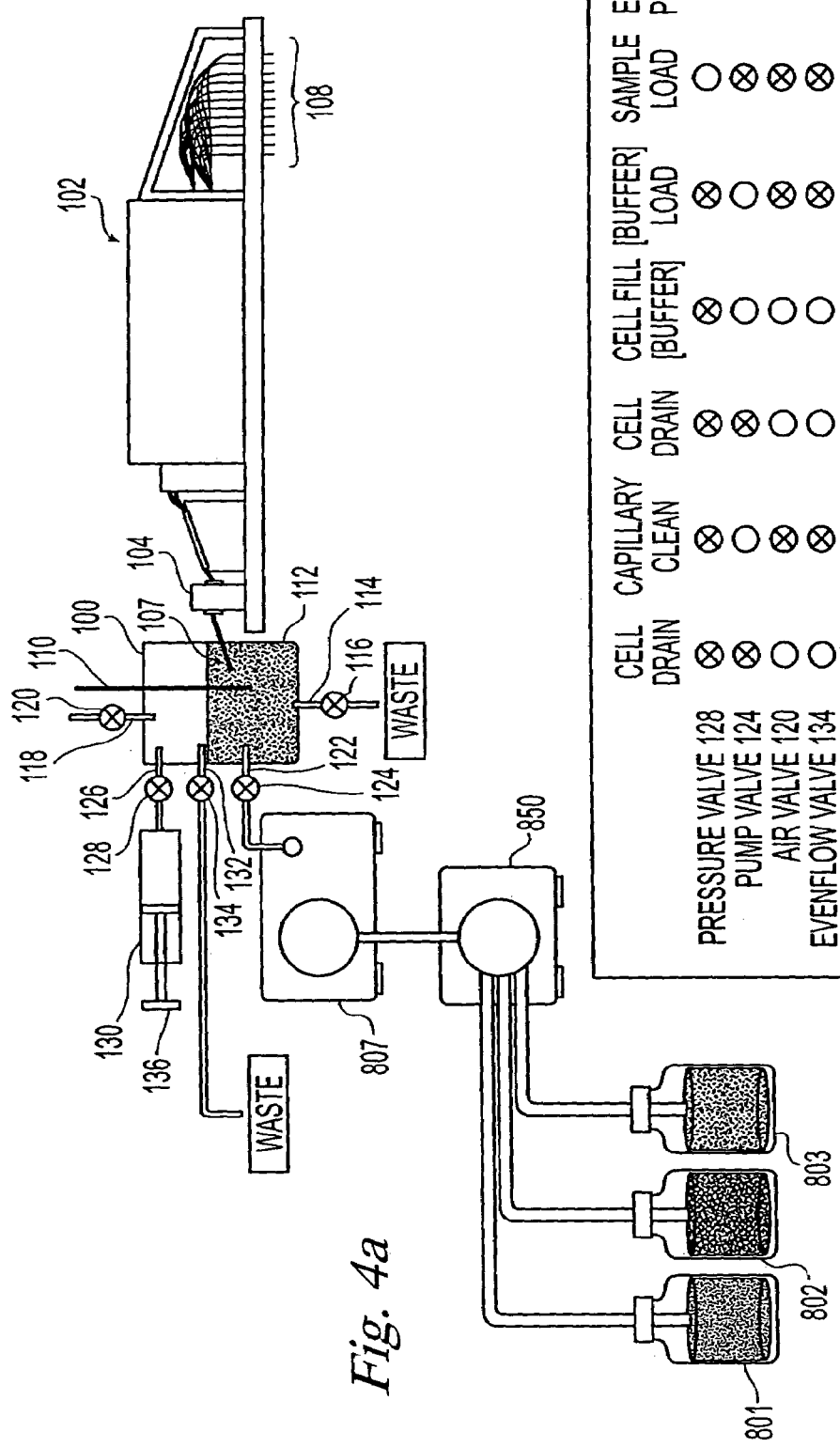

FIG. 4a shows a buffer cell 100 connected to a capillary cartridge 102 via a pressure fitting 104 not unlike that shown in FIG. 3. Indeed, capillary cartridge 102 is similar in structure to the capillary cartridge 1180 of FIG. 3, except that capillary cartridge 102 does not include the T-fitting 1182. In the present invention, the buffer cell 100 and its associated hardware shown in FIG. 4a replace the prior art T-fitting 1182 of FIG. 3 and some of the prior art plumbing system seen in FIG. 2.

The buffer cell 100 has a interior cavity 106 which is which preferably is sealed from the exterior, except for openings discussed below. In the preferred embodiment, the cell is formed from an acrylic plastic, which is an electrical insulating material. Inner walls of the cell are shaped and sized to provide an interior cavity 106 into which a buffer or other liquid 112 may be introduced. In the preferred embodiment, the container has a capacity of about 100 ml, by volume.

A high voltage electrode 110 connected to a power supply (not shown) is in contact with the liquid 112 in the cell 100 for the purpose of applying a predetermined potential to the liquid in the container, and thereby also to the first, cell ends 107 of the capillaries which are in communication with the liquid 112. During CZE, the high voltage electrode 110 is held at ground, while a non-zero voltage is applied to the second, sample ends 108 of the capillaries, with the polarity of the voltage being determined by the charge-type of the samples being separated. The magnitude of the applied voltage is on the order of 10-15 kV, not unlike that used in capillary gel electrophoresis.

A plurality of conduits communicate with the cavity 106 via corresponding valves. In the preferred embodiment, the valves are solenoid valves or the like, which can be controlled by computer, much as discussed in the above-identified U.S. application Ser. No. 09/105,888.In FIG. 4a, each of the five conduits connected to the cell 100, whether it is an inlet or an outlet, or serves as both, is shown to have a separate valve. It is understood, however, that one or more of these valves may be internal to equipment connected to the corresponding conduit, rather than being a discrete valve.

Drain outlet 114 and drain valve 116 allow a liquid in the cavity 106 to exit the cell 100 into a waste container (not shown). Air conduit 118 and gas (air) release valve 120 provide a path from the interior of the cavity 106 to the atmosphere when air valve release 120 is open. Pump inlet 122 and pump valve 124 provide a path for buffers, solvents and other liquids in containers, such as those indicated by 801, 802 and 803, to enter the cell 100 via one or manifolds 850, under assistance of an HPLC pump 807, or the like. Pressure conduit 126 and pressure valve 128 connect a syringe 130 or other pressure applicator to the cavity 106 at a point above the level of liquid 112 therein. Finally, overflow outlet 132 and overflow valve 134 cooperate to provide a passage from the interior of the cavity 106 to a waste container, so as to ensure that the cell 100 does not overfill. While the various valves 116, 120, 124, 128 and 134 are shown to be distinct devices, it should be kept in mind that one or more of these valve may be an integral part of another device. For instance, pump valve 124 may be integrally formed as part of HPLC pump 807, and pressure valve 128 may be replaced by precisely controlling the syringe's piston 136 by a stepper motor, or the like, under the direction of a controller.

FIG. 4a depicts the valve positions for performing steps associated with preparing and conducting electrophoresis on the samples in the capillary tubes of the capillary cartridge 102.

When the cell 100 is to be drained, the pressure valve 128 and the pump valve 124 are closed, and the drain valve 116 and at least one, if not both, of the air valve 120 and the overflow valve 134 are opened. This allows the liquid in the cell to drain via drain conduit 114.

Once the cell 100 has been completely drained, it may be partially filled with a liquid. For this, the drain valve 116 and the pressure valve 128 are closed, and the pump valve 124 and at least one, if not both, of the air valve 120 and overflow valve 134 open. The pump 807 is then operated to introduce a selected one of the liquids in containers 801, 802, 803 into the cell 100. Because the pump introduces liquid into the reservoir and, because at least one of the air valve 120 and the overflow valve 132 is open, the liquid is not forced into the capillaries. However, the pump is controlled to turn off when the liquid reaches a predetermined level within the cell.

When the capillaries are to be cleaned, a cleaning solution, or the like, present in one or more of the containers 801, 802, 803, is forced into the cell 100, into the cell ends 107 of the capillary tubes, and out the sample ends 108 of the capillary tubes. For this, only the pump valve 124 is open while all the other valves are closed. Under such conditions, when the HPLC pump 807 operates, it forces liquid into the cell 106, increasing the pressure therein. The increased pressure forces the cleaning solution into the cell ends 107, through the capillary tubes and out the sample ends 108. Once cleaning solution has been forced through, the pump valve may be closed, and the cell 100 drained, as discussed above.

After cleaning, the cell can be filled with buffer to a predetermined level by selecting the appropriate container 801, 802, 803 with the manifold 850, and operating the pump 807 with the drain valve 116 and the pressure valve 128 closed, and the pump valve 124 and at least one, if not both, of the air valve 120 and overflow valve 134 open. The predetermine level of buffer should exceed the level of the bundle of capillary cell ends 107.

Once the level of the buffer has exceeded the level of the capillary cell ends 107, buffer may be loaded into the capillaries. For this, the only the pump valve 124 is left open, and all other valves are closed. The buffer enters the capillary cell ends 107, thereby forcing any material within the capillary tubes out the capillary sample ends 108 into a waste container (not shown), and loading the capillary tubes with buffer. At this point, the cell 100 is filled with buffer to just below the level of the overflow conduit 132, yet above the level of the capillary cell ends. In the preferred embodiment, the overflow conduit 132 is at about the 60% fill level and so the cell 100, having a capacity of 100 ml, contains approximately 60 ml of buffer.

It should be evident that filling the capillaries with buffer is similar to the procedure for cleaning the capillaries, except that buffer, rather than a cleaning solvent, is used. As discussed above, this is controlled by operating the manifold 850 connected to the containers 80, 802 and 803 holding buffers, cleaning solutions and other liquids. It should be noted, however, that buffer itself can be used to clean the capillaries.

To introduce a sample into the sample ends 108 of the capillaries, the sample ends 108 are first dipped into wells of a microtitre tray of standard size, such as those having a rectangular array of 8 rows of 12 wells, or those having 16 rows of 24 wells. The wells contain the samples to be electrophoresed.

The samples can be introduced into the sample ends 108 of the capillaries in one of two ways. One way is electro-kinetic injection wherein a voltage differential is applied between the sample ends and the cell ends of the capillaries so as to cause a portion of the sample to enter the sample ends. During electro-kinetic injection, the air valve 120 is kept open keep the reservoir 100 at atmospheric pressure, equilibrated with the cell ends 107 of the capillary. By applying a high voltage differential, the electro-osmotic flow causes sample enter the capillary sample ends 108. Once the sample has been introduced into the sample ends from the wells of the microtitre tray, the sample tray is replaced a buffer tray and electrophoretic separation can take place in the capillaries under high voltage.

A second way in which to load samples into the sample ends 108 of the capillaries is by hydrodynamic injection. First, air valve 120 is opened and all other valves are closed to equilibrate both ends of the capillaries with atmospheric pressure. After equilibration, the air valve 120 is also closed, and so no valves are left open. At this point, the plunger 136 of the syringe 130 is pulled back by a predetermined volume. This causes the air above the liquid level in the cell to expand into a slightly greater volume and thereby create a vacuum, or negative pressure. At this point, the pressure valve 128 is opened, thereby applying this negative pressure to the surface of the buffer 112 in the cell 100. Due to the negative pressure, a small amount of sample (or other substance in each of the wells of the microtitre tray) is sucked in at each of the capillary sample ends. However, because air expands to fill the volume, there is a slight time lag between opening the pressure valve 128 and the uptake of sample. After the sample is allowed to enter due to the negative pressure for a predetermined period of time, typically on the order of a few seconds, the air valve 120 is opened, thereby stopping the injection process. Experiments have shown that hydrodynamic injection produces more reproducible results, and more even sample injection into the capillaries. This is because the volume into which the air expands does not immediately cause an instantaneous, corresponding intake of sample at the capillary sample ends, when the pressure valve 126 is opened. Instead, a fairly even uptake into each of the capillary sample results.

The pulling volume of the syringe controls the degree of negative pressure or vacuum. In the preferred embodiment, the plunger is pulled back by an amount sufficient to displace about 2 ml. In a 100 ml container having 60 ml of buffer therein, there is about 40 ml of air. When the plunger is pulled back by 2 ml, a negative pressure (relative to atmospheric) of 2.0 ml/40.0 ml=0.05 atm (or about 0.7 psi) is generated. Assuming a syringe precision of 0.1 ml and a container volume of 100 ml, the precision of the negative pressure can be controlled to about 0.001 atm.

Once the sample has been introduced into the capillary sample ends, the sample tray is preferably replaced by a buffer tray in preparation for electrophoresis. Replacing the sample trays with buffer trays helps ensure than excess sample is not taken into the capillary tubes, and also ensures that both ends of the capillary tubes are inserted into buffer. Using a device in accordance with the present invention, electrophoresis can take place in either a static mode, or a dynamic mode.

In the static mode, the pump 807 is not operational and only the air valve 120, or the overflow valve 134, or both, are open, with the remaining valves closed. Under these conditions, the buffer in the cell 1 12 is substantially stagnant during electrophoresis.

In the dynamic mode, the pressure valve 128 is closed, and all other valves are open, and the pump is operational, with buffer continuously being pumped into the cell through the pump inlet 122 and exiting the cell via drain outlet 114. This ensures that fresh buffer bathes the capillary cell ends during electrophoresis while older buffer drains from the cell. Samples which have completed migrating from the sample end all the way to the cell end are also drained through drain outlet 114 and drain valve 116. At the same time, since air conduit 118 and air valve 120 are open, the atmospheric pressure at both ends of the capillaries is equalized, thereby counteracting the siphoning effect, especially when the capillary ends are at the same height.

The dynamic mode, in which there is continuous flushing of the cell 100, provides several advantages. First, continuously providing fresh buffer solution to the capillary cell ends removes charge depletion during electrophoresis. Charge depletion happens when anion and cation layers build up around the electrode, thereby resulting in a voltage drop between these layers which, in turn, reduces the voltage drop across the capillary tubes for separation. Flowing buffer helps retard the formation of such layers so that sample separation is more reproducible from run to run.

A second advantage to constant flushing is that it assists in removing fluids and contaminants introduced into the cell by electro-osmotic flow (EOF) during electrophoresis. EOF is a continuous pumping process which brings small amounts of sample-laden buffer into the cell. This can cause a change in buffer conductivity during electrophoresis. Constant flushing helps mitigate the problem of a solute-imbalance. Sensors and feedback control systems connected to the pump and to the pump and drain valves can ensure that the liquid level in the cell is maintained at a predetermined level.

A third advantage to continuous flushing is that it reduces the time spent cleaning the capillary tubes between runs. Because fresh buffer is constantly being introduced into the cell in the dynamic mode, one need spend as much time rinsing out the cell, upon conclusion of each run.

A fourth advantage to continuous flushing is that it removes air bubbles which otherwise collect around the capillary cell ends 107 during electrophoresis. Such removal is believed to be brought about by the buffer flowing past this area.

In one example of continuous flushing using capillaries with an inner diameter of 50 µm, a voltage differential of 10 kV across the capillary ends and borate buffer at a pH of 10.5, EOF speed is about 12 cm/min. This causes the liquid volume of the cell to increase at the rate of about 53 µl/min. If a drain is provided, the buffer must be replenished, as needed. In the preferred embodiment, only about 1 ml/min of fresh buffer is introduced into the cell while the drain valve is opened during electrophoresis.

Despite the above-stated advantages, it should be kept in mind that continuous flushing, though preferable, is not an absolute requirement in the present invention. Indeed, the primary requirements for carrying out CZE in accordance with the present invention are that a cell be provided, the cell having a liquid therein with the capillary cell ends terminating in said liquid, and that some mechanism be provided for creating a vacuum, or suction effect, at the capillary cell ends so as to draw samples into capillary sample ends.

Figure 5:
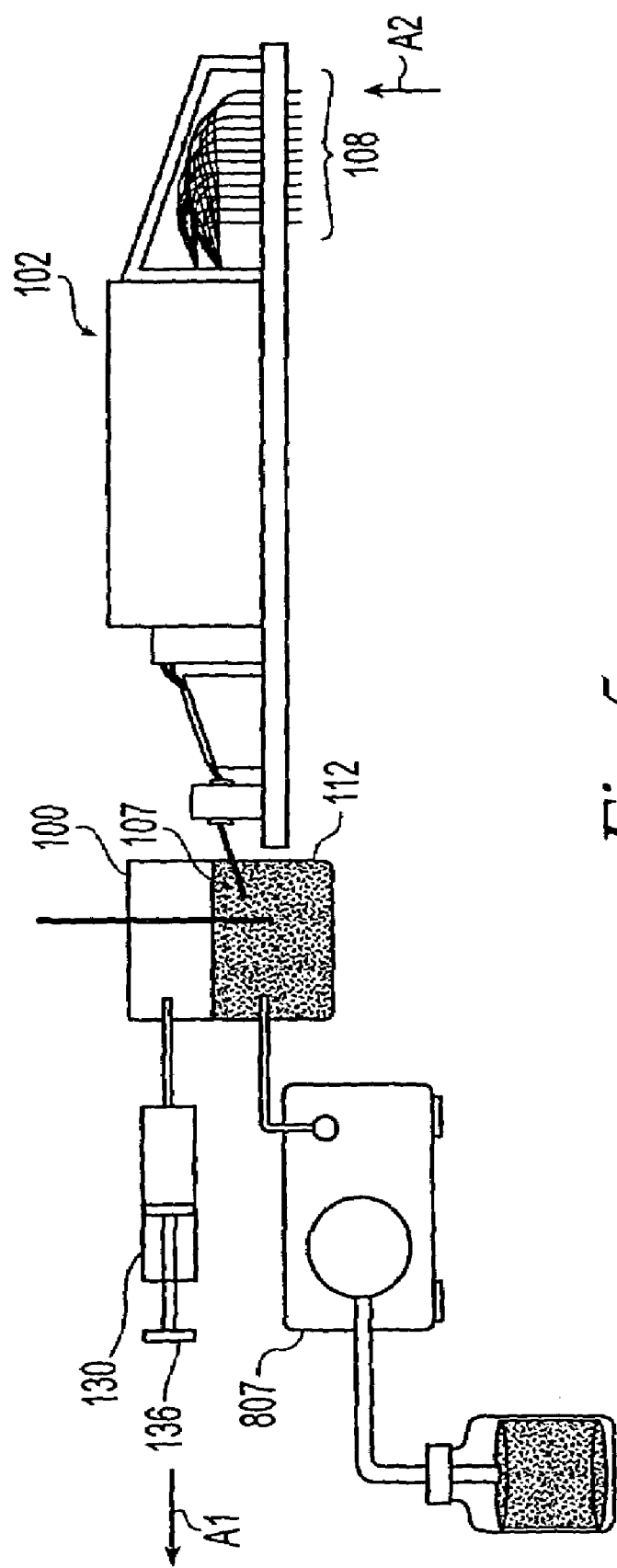
FIG. 5 shows a second embodiment of a system in accordance with the present invention.

FIG. 5 presents another embodiment in accordance with the present invention. In the embodiment of FIG. 5, a sealed, or at least sealable, cell 100 partially filled with a liquid 112 is provided. The capillary cell ends 107 terminate in this liquid 112. An air syringe 130 and an HPLC pump 807 are also provided. When the syringe plunger 136 is pulled in the direction shown by the arrow A1, sample is introduced into the capillary sample ends 108, as depicted by arrow A2. As discussed above with reference to FIG. 4a, conduits for drain, air release and overflow may also be provided. To clean the cell in this embodiment, one simply restrains the syringe plunger and runs the pump to flush out the liquid in the cell and in the capillary tubes via the capillary second ends.

FIG. 6a presents yet another embodiment in accordance with the present invention. In this embodiment, which is similar to embodiment of FIG. 5, the entire cell and the syringe are filled with liquid and no air (or other gas) is used. Unlike air, liquid is incompressible, and so there is neither a time delay nor a variation in volume, between pulling the syringe plunger and the introduction of samples into the capillary sample ends. This means that the syringe must be much more precisely controlled in the embodiment of FIG. 6a than in the embodiment of FIG. 5. For this, a micro-syringes operated by high-precision stepper motors, or the like, is used to ensure that only a small quantity of sample, about 0.1 µl or so, per capillary, is introduced into each of the capillary second ends. To clean the cell and the capillary tubes in the embodiment of FIG. 6a, one may either push on the syringe plunger or run the pump; either one forces buffer into the cell and out through the capillary sample ends.

FIG. 6a presents still another embodiment in accordance with the present invention. In this embodiment, the syringe is replaced by a narrow-diameter drain outlet 140 controlled by a valve 142 situated at a vertical position lower than that of the capillary sample ends 108. In this embodiment, gravity is used to cause a negative pressure. With the pump off, when the valve 142 is opened, liquid drains through the conduit 140 as indicated by arrow A3. This siphons liquid into the capillary sample ends, as indicated by arrow A4.

In the embodiments of FIGS. 5, 6a and 6b, discrete valves between the pump and the cell are not shown; it is understood, however, that such valves may be integral with the pump. Similarly, no such valves are shown between the syringe and the cell. As explained above, the syringe plunger may be restrained and controlled by a motor so as to exert sufficient force in the appropriate direction, as dictated by a microprocessor or other controller. Also, with regard to the embodiments of FIGS. 6a and 6b, it is noted that since only a very minute quantity of liquid is introduced from the capillary tubes into the cell, there is no appreciable increase in pressure within the cell, which is substantially able to accommodate the added amount.

EXPERIMENTAL EXAMPLE

In an experimental set-up, capillary zone electrophoresis was carried out simultaneously in 96 capillaries using a device substantially arranged as shown in FIG. 4a. About 60 ml of buffer was introduced into a 100 ml cell. The buffer used was a 10 mM borate solution in de-ionized water, adjusted to a pH 10.5 with NaOH. The viscosity of the buffer was almost the same as that of water.

Ninety-six capillaries, each having a length of about 50 cm, and ID of 50 µm and an 150 OD µm, available from Polymicro Technology of Phoenix, Ariz. were used. A window region was burned into each capillary using a hot wire at a point approximately 10 cm from one end of the capillaries, thereby providing an effective migration distance of about 40 cm from the sample end to the window region at which sample detection would take place. The capillaries-were arranged substantially parallel to one another in a ribbon-like arrangement. More specifically, for most of their length from the sample ends to the window, the capillaries were spaced apart from one another by about 150 µm and, at the window region, were spaced apart by about 300 µm. Beyond the window region, the cell ends of the 96 capillaries were bound together as a bundle with Torr Seal, available from Varian Vacuum Products of Lexington, Ma. This bundle was connected to the cell shown in FIG. 4a with a Swagelock fitting, with the capillaries being in communication with the buffer. Meanwhile, the sample ends of the capillaries formed a two-dimensional array with a spacing corresponding to that of the wells of an 8×12 microtitre tray of standard size.

A 3 µl sample was introduced into each of the wells of an 8×12 microtitre tray. The sample comprised a protein cluster separated from among a multitude of such clusters in a protein mixture extracted from bacteria. The proteins were labeled with fluorescein dye, which has its absorption maximum at 495 nm. The sample ends of the capillaries were inserted into corresponding wells of the microtitre tray, in contact with the sample therein. Samples in each of the 96 wells were then hydrodynamically injected into the sample ends of the capillaries. This was performed by creating a vacuum by pulling on the syringe plunger to displace a 3 ml volume with all valves closed, and holding the plunger in place. At this point, the pressure valve was opened, thereby causing a negative pressure at the air-buffer interface on the surface of the buffer in the cell. The pressure valve was opened for about 20 seconds, permitting sufficient time for sample to be sucked into each of the capillary sample ends. At this point, the air valve was opened to alleviate the negative pressure and stop further hydrodynamic injection of sample.

Next, the microtitre tray containing samples was replaced with a microtitre tray containing buffer, in preparation for electrophoresis. A voltage differential of 10 kV was applied for about 10 minutes across the 50 cm-long capillaries, thereby providing an electric field of 200 v/cm and causing the samples to migrate under electro-osmotic flow, along with the buffer. An all-line Argon-ion laser, available from Spectra-Physics of Mountain View, Calif., and having an emissions peak not far from 495 μm, was used to illuminate the capillaries substantially at right angles thereto at the window region during electrophoresis. A CCD camera, available from PixelView of Beaverton, Or., was used to detect the fluorescence of the samples as they passed through the window region of the capillaries. The camera was set up substantially as disclosed in co-owned allowed U.S. application Ser. No. 09/084,236, also published as WO 99/32877.

Figure 7:
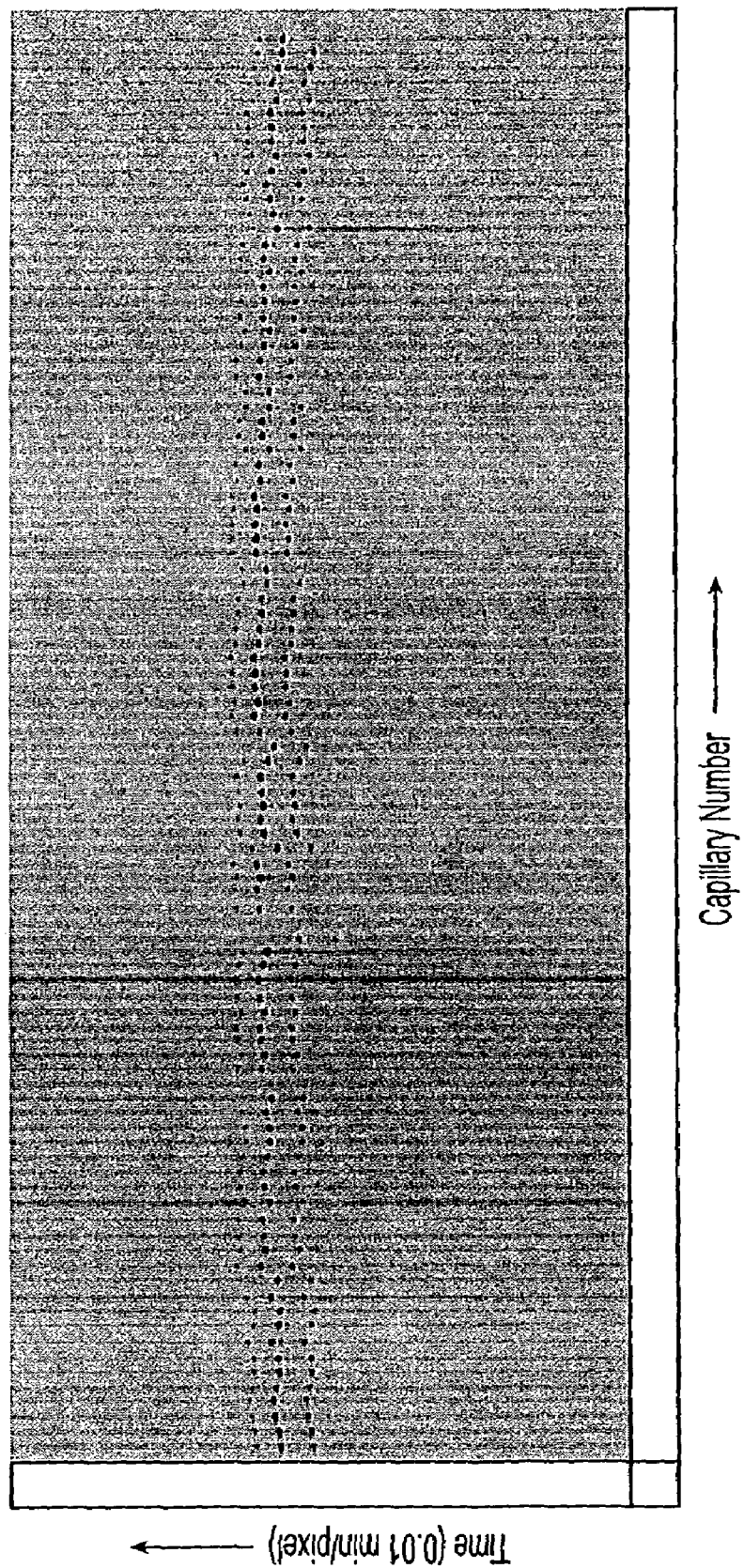
FIG. 7 shows intensity images comprising fluorescence data from experimental samples in 96 capillaries simultaneously migrating.

FIG. 7 shows the fluorescence intensities at 530±8 nm, as a function of time, of the samples in the 96 capillaries, In FIG. 7, the abscissa (x-axis) represents the capillary number while the ordinate (y-axis) represents time. The darker the spot, the higher the intensity.

FIGS. 8a, 8b and 8c show plots of relative intensities for edge and center capillaries (capillary nos. 1, 48 and 96) in the array, as a function of time. In FIG. 8, the abscissa (x-axis) represents time, while the ordinate (y-axis) represents the intensity. As seen in FIG. 8, the intensity contours are substantially the same, exhibiting similar peaks from each capillary, albeit at slightly different migration times for each capillary.

As seen in this experimental example, CZE can be used to separate proteins in a buffer having a predetermined pH. For example, CZE can be used for human growth hormone separation, Ca++ binding protein separation, and recombinant human erythroprotein protein separation, among others. The separation mechanism in CZE is based on the ratio of the net charge to the size of the proteins. The net charge can be of either polarity, depending on the buffer pH and the protein's structure. Electro-osmotic flow of the buffer in the capillaries sweeps neutral molecules, as well as charged proteins, toward the detection window. The buffer preferably has a viscosity about the same as that of water.

The present invention may also be used in other capillary electrophoresis settings in which the separation media has low viscosity, on the order of 1-150, and more preferably on the order of 1-50, centipoise. At these viscosities, the separation media can be pumped into the capillaries under pressure without damage to the capillaries or other components of the system, and the samples injected hydrodynamically. A number of these other approaches and applications are now discussed.

Sodium Dodecyl Sulfate(SDS)-type Capillary Gel(CGE)/NGE (Non-Gel)Electrophoresis. In this approach, the proteins are bound with the surfactant SDS to form negatively charged aggregates. A polymer-based sieving matrix, such as polyethylene oxide(PEO), preferably kept at a low pH to extend the lifetime of the capillaries, is used as the separation medium. Applications for this include peptide mapping, molecular weight estimation, protein quantization and protein stability analysis. In some cases, CGE with a low-viscosity separation media, such as polyvinylpyrrolidone (PVP), which has a viscosity of 1-25 centipoise when in a weight percentage of 0.1-5%, can be used for DNA separation, as reported in Gao & Yeung, Anal. Chem., 1998, v. 70, pp. 1382-1388.

Capillary Iso-Electric Focusing (CIEF), in which the proteins are separated according to their unique iso-electric points in a separation medium having a viscosity similar to that of water, may also be performed using the device and method of the present invention.

Affinity Capillary Electrophoresis (ACE) in which proteins are separated on the basis of specific bonding to other molecules in a separation medium having a viscosity of about 5-50 centipoise may also be performed using the device and method of the present invention.

Micellular Electrokinetic Capillary Chromatography (MEKC) in which compounds are separated based on their hydro-phobicity in a separation medium having a viscosity of about 5-50 centipoise may also be performed using the device and method of the present invention. Such an approach would be especially useful in separating non-charged species.

Capillary Isotachphoresis (CITP), which is used for in-capillary protein pre-concentration, immediately preceding CZE, may be performed using the device and method of the present invention.

While the above invention has been described with reference to certain preferred embodiments, examples and suggested applications, it should be kept in mind that the scope of the present invention is not limited to these. One skilled in the art may find variations of these preferred embodiments which, nevertheless, fall within the spirit of the present invention, whose scope is defined by the claims set forth below.

What is claimed is:

1. A capillary zone electrophoresis subsystem configured to cooperate with a light source and a light detector to detect migrating samples, the subsystem comprising:
    a fluid container
    a plurality of capillary tubes, each capillary tube having a first end and a second end, the first ends being arranged to receive samples thereinto and each of the second ends terminating in the fluid container;
    a power supply configured to apply a voltage across the capillary tubes;
    a pump operably connected to the fluid container, the pump configured to introduce a liquid into the container when the pump is in an operating mode;
    a vacuum device connected to the fluid container via a vacuum conduit entering the fluid container at a level higher than a level of each second end of the capillary tubes, the vacuum device configured to cause a negative pressure in the container, when the pump is not in the operating mode and the container is sealed;
    a gas release valve connected to the container and configured to vent a gas in the container when the gas release valve is opened; and
    a drain valve connected to the container and configured to drain a liquid in the container, when the drain valve is open.

2. The capillary zone electrophoresis subsystem of claim 1, further comprising: an overflow conduit connected to the container, the overflow conduit configured to release liquid held within the container, when a height of the liquid within the container exceeds a predetermined level.

3. The capillary zone electrophoresis subsystem of claim 2, further comprising: an overflow valve positioned in the overflow conduit, the overflow valve having at least a first, open position, and a second, closed position.

4. The capillary zone electrophoresis subsystem of claim 1, wherein the vacuum device is a syringe.

5. The capillary zone electrophoresis subsystem of claim 1, wherein the capillary first ends are arranged in a two-dimensional array having a spacing corresponding to that of wells of a microtitre tray, the system further comprising: a positioning apparatus comprising an upper and a lower carrousel carrying microtitre trays, the positioning apparatus arranged to position one of the microtitre trays such that the two dimensional array of capillary first ends is inserted into corresponding wells of the microtitre tray.

6. The capillary zone electrophoresis subsystem of claim 1, wherein the vacuum device and the pump are separate devices.

7. A capillary zone electrophoresis subsystem configured to cooperate with a light source and a light detector to detect migrating samples, the subsystem comprising:
- a fluid container;
- a plurality of capillary tubes, each capillary tube having a first end and a second end, the first ends being arranged to receive samples thereinto and the second ends terminating in the fluid container;
- a power supply configured to apply a voltage across the first and second ends of the capillary tubes;
- a pump connected to the fluid container, the pump configured to introduce a liquid into the container when the pump is in an operating mode; and
- a vacuum device connected to the fluid container via a vacuum conduit entering the fluid container at a second level higher than a level of each second end of the capillary tubes, the vacuum device configured to cause a negative pressure in the container, when the pump is not in the operating mode and the container is sealed, wherein the vacuum device and the pump are separate devices.

8. The capillary zone electrophoresis subsystem of claim 7, further comprising: a gas release valve connected to the container and configured to vent a gas in the container when the gas release valve is opened.

9. The capillary zone electrophoresis subsystem of claim 8, further comprising: a drain valve connected to the container and configured to drain a liquid in the container, when the drain valve is open.

10. The capillary zone electrophoresis subsystem of claim 9, further comprising: an overflow conduit connected to the container, the overflow conduit configured to release liquid held within the container, when a height of the liquid within the container exceeds a predetermined level.

11. The capillary zone electrophoresis subsystem of claim 10, further comprising: an overflow valve positioned in the overflow conduit, the overflow valve having at least a first, open position, and a second, closed position.

12. The capillary zone electrophoresis subsystem of claim 7, wherein the capillary first ends are arranged in a two-dimensional array having a spacing corresponding to that of wells of a microtitre tray, the system further comprising: a positioning apparatus comprising an upper and a lower carrousel carrying microtitre trays, the positioning apparatus arranged to position one of the microtitre trays such that the two dimensional array of capillary first ends is inserted into corresponding wells of the microtitre tray.

13. The capillary zone electrophoresis subsystem of claim 7, wherein the vacuum device is a syringe.

14. The capillary zone electrophoresis subsystem of claim 7, wherein the vacuum device is a drain conduit provided with a valve member positioned at a height below a height of the capillary first ends, whereby a gravity flow of liquid through the drain conduit by gravity causes a negative pressure in the container, thereby siphoning samples into each of the plurality of capillary tube first ends.

15. A method for capillary zone electrophoresis on a plurality of samples, the method comprising:
- providing a plurality of capillary tubes, each capillary tube having a first end and a second end, the first ends being arranged to receive samples thereinto and the second ends terminating in a fluid container;
- introducing a first liquid into the fluid container to a height at least as high as a level of each second end within the container;
- applying a negative pressure to the capillary second ends to hydrodynamically introduce a sample to be electrophoresced into each of the capillary first ends, wherein the step of applying a negative pressure is performed by a device distinct from that used for the step of introducing a first liquid; and
- applying a voltage differential between the capillary first ends and the capillary second ends to cause the samples to migrate towards the capillary second ends through electro-osmotic flow;
- wherein the step of applying a negative pressure comprises: withdrawing air in the liquid container at a point above a level of the liquid while the container is sealed, thereby causing samples to enter the capillary first ends.

16. The method according to claim 15, wherein the step of withdrawing air comprises: retracting a plunger of a syringe connected to the liquid container.

17. A method for capillary zone electrophoresis on a plurality of samples, the method comprising:
- providing a plurality of capillary tubes, each capillary tube having a first end and a second end, the first ends being arranged to receive samples thereinto and the second ends terminating in a fluid container;
- introducing a first liquid into the fluid container to a height at least as high as a level of each second end within the container;
- applying a negative pressure to the capillary second ends to hydrodynamically introduce a sample to be electrophoresced into each of the capillary first ends, wherein the step of applying a negative pressure is performed by a device distinct from that used for the step of introducing a first liquid;
- applying a voltage differential between the capillary first ends and the capillary second ends to cause the samples to migrate towards the capillary second ends through electro-osmotic flow; and
- flowing a liquid past the capillary second ends while applying the voltage differential.

18. The method according to claim 17, wherein the step of applying a negative pressure comprises withdrawing air in the liquid container at a point above a level of the liquid while the container is sealed, thereby causing samples to enter the capillary first ends.

19. The method according to claim 18, wherein the step of withdrawing air comprises: retracting a plunger of a syringe connected to the liquid container.

20. The method according to claim 17, wherein the step of applying a negative pressure comprises draining a portion of a liquid in the liquid container, such that samples are siphoned.

* * * * *